United States Patent [19]

Tokitoh et al.

[11] Patent Number: 5,057,631

[45] Date of Patent: Oct. 15, 1991

[54] PROCESS FOR CONTINUOUS PRODUCTION OF OCTA-2,7-DIEN-1-OL

[75] Inventors: Yasuo Tokitoh; Noriaki Yoshimura, both of Kurashiki, Japan

[73] Assignee: Kuraray Co., Ltd., Kurashiki, Japan

[21] Appl. No.: 478,744

[22] Filed: Feb. 12, 1990

Related U.S. Application Data

[63] Continuation of Ser. No. 181,163, Apr. 13, 1988, abandoned.

[30] Foreign Application Priority Data

Apr. 16, 1987 [JP] Japan .................................. 62-94668
Apr. 16, 1987 [JP] Japan .................................. 62-94669

[51] Int. Cl.$^5$ ...................... C07C 29/44; C07C 29/36; C07C 33/02
[52] U.S. Cl. .................................. 568/909.5; 568/903
[58] Field of Search ...................................... 568/909.5

[56] References Cited

U.S. PATENT DOCUMENTS 4,142,060  2/1979  Kuntz .................................. 568/657
4,417,079  11/1983  Yoshimura et al. .............. 568/909.5

*Primary Examiner*—J. E. Evans
*Attorney, Agent, or Firm*—Oblon, Spivak, McClelland, Maier & Neustadt

[57] ABSTRACT

Butadiene and water are reacted continuously in the presence of a solvent capable of dissolving both reactants and a palladium catalyst with the mole ratio of butadiene to the reaction product octa-2,7-dien-1-ol in the reaction mixture being maintained at 0.6 or more. By this process, octa-2,7-dien-1-ol can be produced continuously without reductions in reaction rate and selectivity and with decreased insoluble polymer formation.

18 Claims, No Drawings

PROCESS FOR CONTINUOUS PRODUCTION OF OCTA-2,7-DIEN-1-OL

This application is a continuation of application Ser. No. 07/181,163, filed on Apr. 13, 1988, now abandoned.

BACKGROUND OF THE INVENTION

1. Field of the Invention

The present invention relates to a process for continuous production of octa-2,7-dien-1-ol comprising reacting butadiene with water.

2. Description of the Related Art

For the production of octa-2,7-dien-1-ol by reacting butadiene with water in the presence of a palladium catalyst, there are several alternative processes. In one of these known processes, butadiene and water are reacted in a co-solvent for both reactants, such as tetrahydrofuran, isopropyl alcohol or tertbutanol in the presence of a catalyst comprising tetrakis(triphenylphosphine) palladium (U.S. Pat. No. 3,670,032). In another process, butadiene and water are reacted in a solvent which is at least partially miscible with both reactants in the presence of a palladium compound complexed with a phosphine ligand such as triphenylphosphine and carbon dioxide to give octa-2,7-dien-1-ol (U.S. Pat. No. 3,992,456). In these processes, the product octa-2,7-dien-1-ol can be separated from the reaction mixture by subjecting the palladium-containing reaction mixture to distillation. However, a detailed study by the present inventors revealed that when the distillation temperature exceeds about 120° C., the palladium catalyst tends to be decomposed to the metal and inactivated. As a production process in which the product octa-2,7-dien-1-ol can be separated from the reaction mixture without resort to distillation, there is a process in which butadiene and water are reacted in the system containing palladium acetate and trisodium salt of tris(m-sulfophenyl)phosphine and the organic phase containing the reaction product is separated from the aqueous phase containing the catalyst by decantation (U.S. Pat. No. 4,142,060). However, because of the extremely poor solubility of butadiene in water, this process has the disadvantage of very low reaction rate and low selectivity to octa-2,7-dien-1-ol.

Since any palladium catalyst of the type which is used in reactions for synthesis of octa-2,7-dien-1-ol are quite expensive catalysts as is well known, the following technical objectives must be achieved in order to produce octa-2,7-dien-1-ol at low cost on a large commercial scale.

1) To achieve a high reaction rate at a commercially permissible palladium catalyst concentration [about several milligram atoms as palladium atom per liter of reaction mixture];

2) To assure a sufficiently high selectivity to octa-2,7-dien-1-ol;

3) To assure that the catalytic activity of the palladium catalyst is maintained over a long time; and 4) To assure that the product octa-2,7-dien-1-ol can be efficiently separated without entailing a deactivation of the palladium catalyst.

To achieve the above technical objectives, two researchers including one of the present inventors have already proposed the following process for producing octa-2,7-dien-1-ol: a process for preparing octa-2,7-dien-1-ol comprising the steps of:

(i) reacting butadiene with water in an aqueous sulfolane solution having a water/sulfolane weight ratio in the range of 20/80 to 70/30 and containing carbonate ions, bicarbonate ions or mixtures thereof, in the presence of (A) palladium or a palladium compound, (B) a monodentate phosphine in an amount of at least 6 moles per gram atom of said palladium; and (C) a monodentate tertiary amine having a basicity constant (pKa) of at least 7 in an amount of 1 to 50% by volume based on the sulfolane to form octa-2,7-dien-1-ol;

(ii) extracting at least part of the reaction mixture obtained in step (i) with a saturated aliphatic hydrocarbon, a monoolefinic hydrocarbon or an alicyclic hydrocarbon; and (iii) recycling at least part of the extraction residue obtained in step (ii) which contains the catalyst components to step (i) (U.S. Pat. No. 4,356,333 and U.S. Pat. No. 4,417,079).

According to the above process described in U.S. Pat. No. 4,356,333 and U.S. Pat. No. 4,417,079, octa-2,7-dien-1-ol can be produced with high reaction rate and selectivity in a low palladium catalyst concentration and, in addition, can be separated from the reaction mixture without entailing a deactivation of the palladium catalyst, thus permitting re-use of the catalyst by recycling. However, even this improved production process has been found to have several drawbacks which must be surmounted in long-term continuous operation. Thus, it is commercially more efficient, from the standpoint of the ease of recovery of unreacted butadiene and isolation of the product, to increase the conversion of butadiene and the concentration of the product in the reaction mixture as much as possible but actually when the reaction is carried out continuously, there take place a progressive accumulation of insoluble polymer in the reaction system, decreases in selectivity to octa-2,7-dien-1-ol and in reaction rate, and inactivation of the palladium catalyst, all of which were almost negligible in the batch reaction or in a semicontinuous operation up to tens of repeated runs, and these phenomena have been found to seriously interfere with the continuous production of octa-2,7-dien-1-ol. It has also been found that when an extractive procedure is adopted for the separation of octa-2,7-dien-1-ol from the reaction mixture in the process of continuous production of octa-2,7-dien-1-ol under conditions conducive to increased butadiene conversion, the amount of dissolution of the palladium catalyst into the extractant solvent increases with time.

SUMMARY OF THE INVENTION

It is an object of the present invention to provide a process for continuous production of octa-2,7-dien-1-ol without entailing decreases in reaction selectivity and reaction rate and, further, with an effective suppression of insoluble polymer formation.

It is another object of the invention to provide a process for continuous production of octa-2,7-dien-1-ol without entailing a loss or inactivation of the palladium catalyst.

It is still another object of the invention to provide a process for continuous production of octa-2,7-dien-1-ol under stable operating conditions over a long period of time.

These objects as well as other objects and advantages of the present invention will become apparent to those skilled in the art from the following description.

The present invention is thus directed to a process for continuous production of octa-2,7-dien-1-ol comprising reacting butadiene with water in a solvent which is capable of dissolving both reactants at least partially in the presence of a palladium catalyst with the mole ratio of butadiene to octa-2,7-dien-1-ol in the reaction mixture being maintained at 0.6 or more.

DETAILED DESCRIPTION OF THE INVENTION

In the production process according to the invention, it is essential that the reaction is carried out with the mole ratio of butadiene to octa-2,7-dien-1-ol in the reaction mixture being maintained at 0.6 or more and preferably at 0.8 or more. In the continuous reaction of butadiene with water, the concentration of the product octa-2,7-dien-1-ol is of course low during the initial phase of the reaction up to establishment of the steady state so that the reaction proceeds with a large excess of butadiene relative to octa-2,7-dien-1-ol. However, after the steady state has been established, the reaction is conducted with the concentrations of butadiene to octa-2,7-dien-1-ol being maintained at the above-mentioned mole ratio. If the mole ratio of butadiene to octa-2,7-dien-1-ol is smaller than 0.6, the accumulation of insoluble polymer in the reaction mixture is favored, the inactivation of the palladium catalyst increased, and both the reaction rate and selectivity decreased by degrees. Moreover, when the extractive procedure is adopted for separation of octa-2,7-dien-1-ol from the reaction mixture, the amount of dissolution of the palladium catalyst into the extractant solvent is encouraged. On the other hand, when the mole ratio of butadiene to octa-2,7-dien-1-ol is too high, the amount of recovery of butadiene and the required capacity of reaction equipment are increased, thus causing economic disadvantages. Furthermore, when the extractive procedure is utilized for separating octa-2,7-dien-1-ol from the reaction mixture, the amount of dissolution of the reaction solvent into the extractant solvent tends to increase. From this reaction, it is desirable to conduct the reaction while the mole ratio of butadiene to octa-2,7-dien-1-ol is maintained in the range of 0.6 to 2.5, more preferably in the range of 0.7 to 2.0 and for still better results in the range of 0.8 to 1.6.

The concentration of butadiene in the reaction mixture in the process of the invention is selected in consideration of the mole ratio of butadiene to octa-2,7-dien-1-ol and the solubility of butadiene in the reaction mixture. From the standpoint of reaction rate and the concentration of octa-2,7-dien-1-ol in the reaction mixture, the concentration of butadiene is preferably maintained at 0.6 mole or more per liter of the reaction mixture. While there is no critical upper limit to the concentration of butadiene, it is generally preferable that the butadiene concentration be not more than 5 moles per liter of the reaction mixture. When the continuous production process of the invention is applied to a reaction system comprising a reaction stage, an extraction stage and a catalyst recycling stage such as the system described in U.S. Pat. No. 4,356,333 and U.S. Pat. No. 4,417,079, the butadiene concentration is preferably maintained in the range of 0.6 to 2.0 moles per liter of the reaction mixture. If the butadiene concentration exceeds 2.0 moles/liter, the reaction mixture may become heterogeneous and the amount of dissolution of the reaction solvent, etc. into the extractant solvent in the extraction stage following the reaction stage for synthesis of octa-2,7-dien-1-ol tends to increase.

The starting material butadiene may be any of the commercially available butadiene, for example, a polymerization grade or chemical reaction grade butadiene or a hydrocarbon mixture which is generally known as the $C_4$ fraction in the petrochemical industry. However, when the height of the reaction rate and the ease of recovery of unreacted butadiene are taken into consideration, the use of the polymerization grade or chemical reaction grade butadiene is preferred.

The solvent which is capable of dissolving both butadiene and water at least partially, which is used in the reaction according to the invention, includes the following species, among others: ethers such as diethyl ether, dibutyl ether, tetrahydrofuran, dioxane, dioxolane, ethylene glycol dimethyl ether, polyethylene glycol dimethyl ether with an average molecular weight of 200 to 2,000, etc.; secondary or tertiary alcohols such as t-butanol, isopropyl alcohol, etc.; ketones such as acetone, methyl ethyl ketone, methyl isobutyl ketone, etc.; nitriles such as acetonitrile, benzonitrile, propiononitrile, etc.; carboxamides such as acetamide, propionamide, N,N-dimethylformamide, N,N-dimethylacetamide, etc.; sulfoxides such as dimethyl sulfoxide etc.; sulfones such as sulfolane, methylsulfolane, etc.; phosphoramides such as hexamethylphosphoramide etc.; esters such as methyl acetate, ethyl acetate, methyl benzoate, etc.; aromatic hydrocarbons such as benzene, toluene, xylene, ethylbenzene, etc.; aliphatic hydrocarbons such as butene, butane, hexane, etc.; and alicyclic hydrocarbons such as cyclohexane, methylcyclohexane, etc.; and so on. The solvent is generally used singly but may be a mixture of two or more species. When the extractive procedure is used for separating the product octa-2,7-dien-1-ol from the reaction mixture, it is important that the amount of dissolution of the reaction solvent, etc. into the extractant solvent be kept as low as possible and from this point of view, it is preferable to use an aprotic polar solvent whose dielectric constant is within the range of 39 to 100, such as sulfolane, methylsulfolane, dimethyl sulfoxide, ethylene carbonate or the like. Moreover, when such factors as long-term stability in the reaction system and the improvement in reaction rate are taken into consideration, the use of sulfolane is particularly beneficial.

In conducting the reaction according to the invention, the addition of the carbonate and/or bicarbonate of a monodentate tertiary amine having a basicity constant (pKa) of not less than 7 to the reaction system is preferred because it leads to a marked enhancement of reaction rate with the selectivity to octa-2,7-dien-1-ol being kept at a high level, a more effective suppression of inactivation of the palladium catalyst, and an increase in the extraction yield of octa-2,7-dien-1-ol in the extraction stage in the case where the extractive procedure is adopted for separation of octa-2,7-dien-1-ol from the reaction system. As specific examples of said monodentate tertiary amine, there may be mentioned trimethylamine, triethylamine, tri-n-butylamine, 1-N,N-dimethylamino-2-propanol, N,N-dimethyl-2-methoxyethylamine, N-methylmorpholine, N,N,N',N'-tetramethylhexamethylenediamine, and so on. Of these species, triethylamine is the most desirable in terms of results of reaction, boiling point, solubility, price and so forth. The above excellent effect obtainable by the addition of the carbonate and/or bicarbonate of a monodentate tertiary amine cannot be obtained with the carbonate and/or bicarbonate of a monodentate or bidentate tertiary amine having a pKa value of less than 7, such as pyridine or dipyridyl, or with the carbonate and/or bicarbonate of a tertiary amine having a strong bidentate property even if its pKa value is not less than 7, such as N,N,N',N'-tetramethyldiaminoethane or N,N-dimethyl-2-aminopropiononitrile.

The carbonate and/or bicarbonate of a monodentate tertiary amine with a pKa value not less than 7 exists in the reaction system as an equilibrium mixture of the carbonate and/or bicarbonate ion and the monodentate tertiary amine (as shown by the equilibrium formula below) and the relative amount of the carbonate and/or bicarbonate of tertiary amine under the reaction conditions is dependent on the temperature and the carbon dioxide partial pressure.

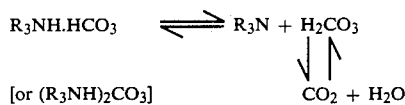

Therefore, the reaction is generally conducted at elevated pressure so as to assure a carbon dioxide partial pressure of about 1 to 20 kg/cm² (absolute pressure). In consideration of results of reaction, extraction efficiency, the amount of dissolution of the tertiary amine into the extractant solvent and so on, it is recommended to use said carbonate and/or bicarbonate of monodentate tertiary amine in an amount assuring a concentration of 5 to 30 weight percent in the reaction mixture.

The water present together with the solvent in the reaction system is consumed as the reaction proceeds. When the extractive procedure is used for separating the product octa-2,7-dien-1-ol from the reaction mixture, the water is desirably present in homogeneous mixture with the solvent in the reaction system. The reaction rate tends to be higher with a decreasing concentration of water in such solvent-water solution, while an increased water concentration leads to a higher extraction rate of octa-2,7-dien-1-ol from the reaction mixture and a tendency of decrease in the amount of dissolution of the reaction solvent and catalyst components into the extractant solvent. In consideration of the above, the weight ratio of water to the solvent in the reaction mixture is generally maintained in the range of 70/30 to 30/70 and preferably within the range of 60/40 to 40/60. It is also preferable that the concentration of water in the reaction mixture be maintained in the range of 25 to 55 weight percent.

In the practice of the invention, the concentration of octa-2,7-dien-1-ol in the reaction mixture can be increased up to about 5 moles per liter insofar as the mole ratio of butadiene to octa-2,7-dien-1-ol in the reaction mixture is maintained at 0.6 or more but when the extractive procedure is to be adopted for separation of octa-2,7-dien-1-ol, it is preferably maintained in the range of 0.3 to 1.5 moles per liter of the reaction mixture in order to assure a high extraction rate of octa-2,7-dien-1-ol, a low level of dissolution of the reaction solvent, etc. into the extractant solvent, and high productivity in commercial operation.

The palladium catalyst to be present in the reaction system in the practice of the invention is an active species derived from a palladium compound. There is no particular limitation on the type of palladium compound that can be used for the preparation of the palladium catalyst. For example, those palladium compounds which have heretofore been proposed for use in the synthesis reaction for octa-2,7-dien-1-ol can be employed successfully. Such palladium compounds include, among others, bis(acetylacetonato)palladium, π-allylpalladium acetate, -allylpalladium chloride, palladium acetate, palladium carbonate, palladium nitrate, palladium chloride, sodium chloroparadate, bis(benzonitrile)palladium chloride, bis(triphenylphosphine)-palladium chloride, bis(triphenylphosphine)palladium acetate, bis(1,5-cyclooctadiene)palladium, bis-π-allyl-palladium and so on. The true palladium catalyst for the synthesis of octa-2,7-dien-1-ol is a palladium complex of low valence and, therefore, when a divalent palladium compound is employed, the effective palladium catalyst can be formed by reducing the compound with the butadiene or monodentate phosphine present in the reaction system. As an alternative, the divalent palladium compound may be reacted with a reducing agent in the same reaction vessel or an independent reaction vessel to prepare the necessary palladium catalyst. The reducing agent which may be used for this purpose includes, among others, alkali metal hydroxides, alkali metal carboxylates, sodium borohydride, zinc dust, magnesium, hydrazine and so on. There is no particular limitation on the amount of palladium catalyst to be made available in the reaction system but for commercial scale production, the concentration of palladium catalyst may preferably be 0.1 to 50 milligram atoms and, for still better results, 0.5 to 5 milligram atoms as palladium atom per liter of the reaction mixture.

The presence of a monodentate organophosphorus compound in the reaction system according to this invention contributes to a greater stability of the palladium catalyst and, in certain circumstances, to a higher selectivity of the reaction. The monodentate organophosphorus compound is used preferably in a proportion of at least 6 moles per gram atom of palladium and, for still better results, in a proportion not less than 10 moles on the same basis. There is no critical upper limit to the amount of the monodentate organophosphorus compound but such compound is generally used in a proportion of not more than 150 moles per gram atom of palladium and preferably in a proportion not exceeding 80 moles on the same basis. As examples of said monodentate organophosphorus compound, there may be mentioned organophilic (lipophilic) monodentate organophosphorus compounds such as organophilic monodentate phosphines, e.g. triphenylphosphine, tritolylphosphine, etc., and hydrophilic monodentate organophosphorus compounds such as hydrophilic monodentate phosphines. When the hydrophilic monodentate organophosphorus compound is employed, the catalyst and the reaction product can be separated from the reaction mixture by extraction. As examples of the hydrophilic monodentate phosphine, there may be mentioned monodentate phosphines of the general formula:

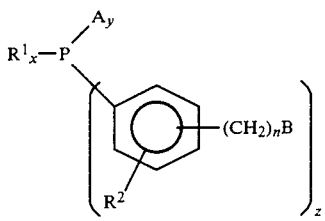

wherein $R^1$ is an aliphatic, alicyclic, or unsubstituted or substituted aromatic hydrocarbon group having 1 to 8 carbon atoms; $R^2$ is a hydrogen atom, a methyl, nitro, cyano or methoxy group or a halogen atom; n represents an integer of 0 or 1; x represents an integer of 0, 1 or 2; y and z each represents an integer of 0, 1, 2, or 3 (provided that y and z are not concurrently equal to 0 and that $x+y+z=3$); A is

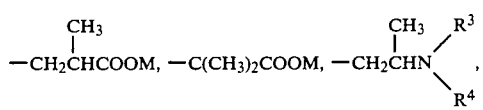

a carbonate or bicarbonate of

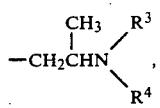

or a carbonate or bicarbonate of

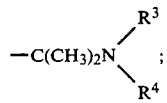

B is —SO$_3$M, —COOM,

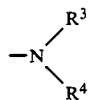

or a carbonate or bicarbonate of

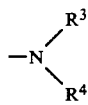

(wherein $R^3$ and $R^4$ each represents a methyl, ethyl or n-propyl group; M is an alkali metal).

Referring to the above general formula (I), the $C_{1-8}$ aliphatic hydrocarbon group represented by $R^1$ may for example be methyl, ethyl, n-propyl, isopropyl, n-butyl, t-butyl, n-octyl or the like. The $C_{1-8}$ alicyclic hydrocarbon group, also designated by $R^1$, may for example be cyclohexyl, methylcyclohexyl or the like. The $C_{1-8}$ aromatic hydrocarbon group designated by $R^1$ may for example be phenyl, benzyl, tolyl, or the like. This aromatic hydrocarbon group may be substituted by methoxy, chloro, cyano, nitro and so on.

Referring to —SO$_3$M and —COOM, represented by B in general formula (I), M is an alkali metal which is preferably sodium, potassium or lithium. The monodentate phosphine of general formula (I) wherein B is —SO$_3$M or —COOM is generally used in the form of an alkali metal salt. It is possible to use the corresponding carboxylic acid, sulfonic acid or ester thereof instead and react it with a salt, e.g. hydroxide, bicarbonate or carbonate, of an alkali metal in the reaction system or an independent reaction vessel to give the desired alkali metal salt. Of the monodentate phosphines of general formula (I), particularly preferred are diaryl or triaryl phosphines of formula (I) wherein $R^1$ is an aromatic hydrocarbon group; n is an integer of 0 or 1; x is an integer of 0, 1 or 2; y is an integer of 0 or 1; z is an integer of 0, 1, 2 or 3 (provided that y and z are not concurrently equal to 0 and that $x+y+z=3$); A is

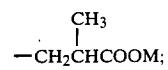

and B is —SO$_3$M, —COOM,

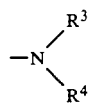

or a carbonate or bicarbonate of

The following is a partial listing of such phosphines.

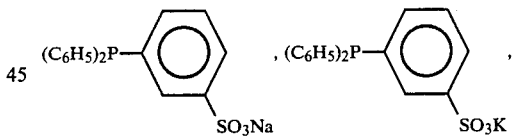

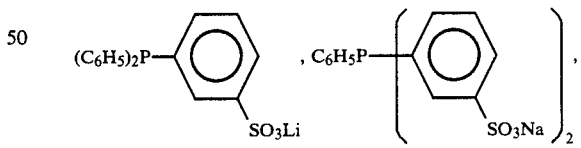

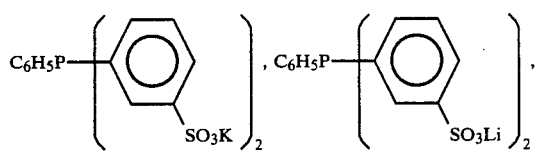

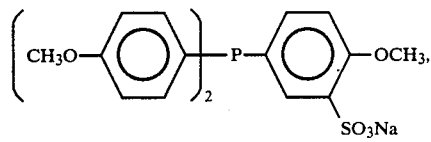

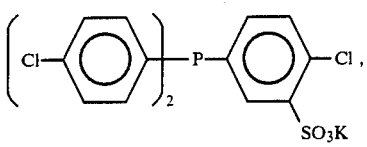

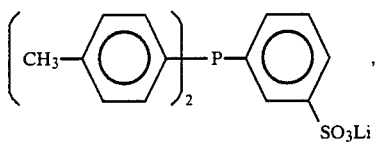

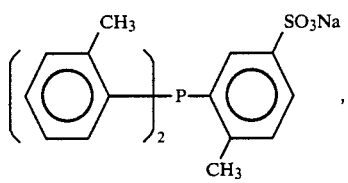

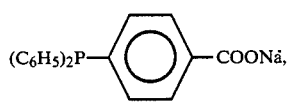

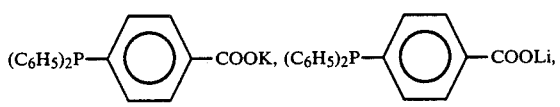

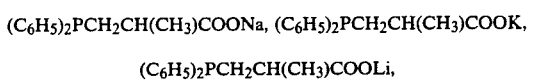

$(C_6H_5)_2PCH_2CH(CH_3)COOLi,$

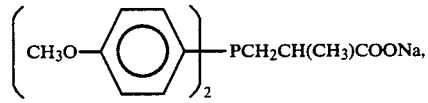

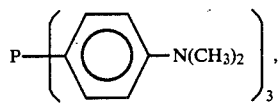

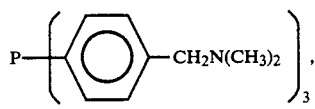

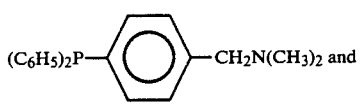

$(C_6H_5)_2PCH_2CH(CH_3)N(C_2H_5)_2$

Of these phosphines, particularly preferred hydrophilic monodentate phosphines are as follows.

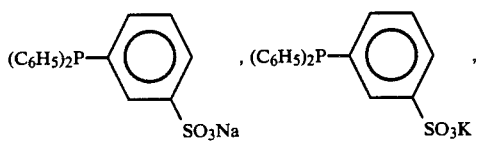

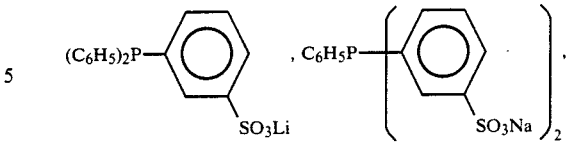

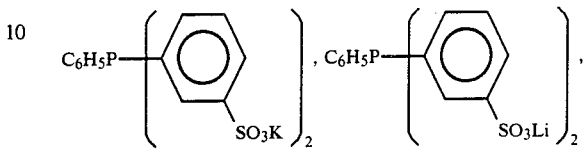

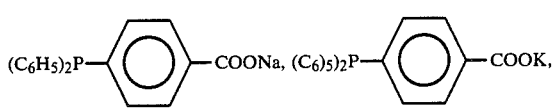

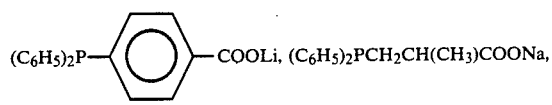

$(C_6H_5)_2PCH_2CH(CH_3)COOK$ and $(C_6H_5)_2PCH_2CH(CH_3)COOLi$

Among the hydrophilic monodentate phosphines of general formula (I), amino-containing phosphines are used in the presence of carbonic acid. The monodentate organophosphorus compounds may be used singly or in combination.

It has been suggested that the addition of a phosphine to the reaction system in excess of 5 moles per gram atom of palladium results in a drastic reduction in reaction velocity with an accompanying decrease in the selectivity of the reaction to octa-2,7-dien-1-ol [Chem. Commun., 330 (1971)]. However, by using a hydrophilic monodentate organophosphorus compound in combination with an aprotic polar solvent having a dielectric constant of 39 to 100, it is possible to maintain the reaction rate and selectivity at high levels even in the presence of a large excess of the organophosphorus compound over the palladium. The use of a large excess of a hydrophilic monodentate organophosphorus compound over palladium in combination with an aprotic polar solvent having a dielectric constant of 39 to 100 not only contributes to a long-term stability of the palladium catalyst activity but is effective in suppressing dissolution of the palladium catalyst into the extractant solvent when an extractive procedure is employed for separating the product octa-2,7l-dien-1-ol from the reaction mixture.

The reaction is generally conducted in the temperature range of 50° to 110° C. The reaction vessel may be a per se known equipment of the gas-liquid contact type, such as a stirring type reactor, a bubble type reactor or the like.

In the process according to the invention, the product octa-2,7-dien-1-ol can be separated by distillation of the reaction mixture at a comparatively low temperature of 80° C. or less but, depending on distilling conditions, the palladium catalyst may be deactivated by degradation or metallization. Therefore, in order that octa-2,7-dien-1ol may be produced under stable conditions over a long run, separation of octa-2,7-dien-1-ol from the reaction mixture is preferably effected by extraction. In this case, octa-2,7-dien-1-ol can be isolated from the extract by a per se conventional separation means such as distillation.

When an extractive procedure is thus adopted, the extraction equipment may be an extraction column conventionally employed in the commercial extraction procedure such as stirring type extraction column, RDC extraction column or perforated plate column. It is commercially advantageous to perform continuous extraction by means of an RDC extraction column.

The extraction is generally carried out in carbon dioxide gas, an inert gas such as nitrogen, helium or argon gas, or a mixture of carbon dioxide gas with such an inert gas. The extraction in carbon dioxide gas or a mixture thereof with an inert gas is effective in suppressing dissolution of the catalyst components and monodentate tertiary amine, which is optionally used, into the extractant. Particularly when a continuous extraction system is employed, extraction is preferably conducted under pressure in an atmosphere of carbon dioxide gas or a mixture thereof with an inert gas. Thus, as the carbon dioxide partial pressure in the extraction system is increased, the effect of controlling the sequential increase in the amount of dissolution of the catalyst components and of the monodentate tertiary amine which is optionally used in combination becomes more remarkable. As the carbon dioxide partial pressure exceeds 3 kg/cm$^2$ (absolute pressure), not only the amounts of catalyst components and tertiary amine lost into the extract are maintained at low levels but the interface between the aqueous layer containing the palladium catalyst and the organic layer containing the product octa-2,7-dien-1-ol is made more discrete. When the carbon dioxide partial pressure is 4 kg/cm$^2$ (absolute pressure) or higher, both the effect of suppressing the sequential increase of dissolution of the catalyst components and tertiary amine and the effect of improving the above-mentioned interface are more remarkably improved. When the carbon dioxide partial pressure exceeds 16 kg/cm$^2$ (absolute pressure), the above-mentioned effects are fully obtained but any further elevation of carbon dioxide partial pressure will not be repaid by any further improvement in these effects. When the carbon dioxide partial pressure is 20 kg/cm$^2$ (absolute pressure) or higher, then the additional consumption of carbon dioxide gas incurs only an economic burden. Therefore, the continuous extraction procedure is preferably conducted in an atmosphere wherein the carbon dioxide partial pressure is higher than 3 kg/cm$^2$ (absolute pressure) and lower than 20 kg/cm$^2$ (absolute pressure), more preferably in the carbon dioxide partial pressure range of 3.5 to 18 kg/cm$^2$ (absolute pressure) and still more desirably in the range of 4 to 16 kg/cm$^2$ (absolute pressure).

The extraction is generally conducted at a temperature not exceeding 60° C. When a continuous extraction system is employed, the lower the extraction temperature, the more inhibited is the decomposition loss f the product octa-2,7-dien-1-ol during extraction and the greater is the tendency of suppression of the sequential increase in the amounts of dissolution of the catalyst components and of the monodentate tertiary amine which has been optionally employed. Conversely, the higher the extraction temperature, the more satisfactory is the phase separation of the aqueous and organic layers. Therefore, the extraction temperature is preferably in the range of 0° to 40° C. and, for still better results, in the range of 5° to 30° C.

The solvents which can be used as said extractant are saturated aliphatic hydrocarbons, monoolefinic hydrocarbons and alicyclic hydrocarbons boiling at temperatures below the boiling point of octa-2,7-dien-1-ol. Thus, there may be mentioned, among others, such saturated aliphatic hydrocarbons as n-butane, isobutane, n-pentane, n-hexane, n-heptane, n-octane, isooctane, etc.; such monoolefinic hydrocarbons as butene, isobutene, etc.; and such alicyclic hydrocarbons as cyclohexane, cyclohexene, methylcyclohexane and so on. The hydrocarbon mixture of butane, butene, isobutene, etc in the C$_4$ fraction used as a butadiene source can also be utilized. Particularly preferred, among these extractants, is n-hexane. The above-mentioned extractants can be used singly or in combination. In consideration of the efficiency of extraction of octa-2,7-dien-1-ol and for suppressing the amounts of dissolution of the catalyst components and reaction solvent into the extract, the extractant is used in a proportion by volume of 0.3 to 3 relative to the volume of the reaction mixture obtained by the reaction for synthesis of octa-2,7-dien-1-ol. The aqueous layer containing the catalyst, which is an extraction residue, can be recycled to the reaction step for synthesis of octa-2,7-dien-1-ol. If desired, part of this residual water layer may be withdrawn and, after catalyst reactivation treatment, be recycled to the reaction step for synthesis of octa-2,7-dien-1-ol.

By the above extraction procedure, the reaction product and byproducts (octa-2,7-dien-1-ol, octa-1,7-dien-3-ol, dioctadienyl ether, octa-1,3,7-triene, highboiling byproducts, etc.) are predominantly separated into the extract. The extract may further contain the unreacted butadiene and small amounts of the reaction solvent, palladium catalyst, water, monodentate tertiary amine, organophosphorus compound and so on. The extract obtained by the above extraction procedure is washed with water to re-extract the reaction solvent, palladium catalyst and other water-soluble substances from the extract. The resulting aqueous layer containing such water-soluble substances can be utilized for the reaction for synthesis of octa-2,7-dien-1-ol.

When the reaction for synthesis of octa-2,7-dien-1-ol is conducted in the presence of the carbonate and/or bicarbonate of a monodentate tertiary amine, when the extraction is conducted in an atmosphere of carbon dioxide gas or a mixture thereof with an inert gas, preferably in an atmosphere such that the carbon dioxide partial pressure is higher than 3 kg/cm$^2$ (absolute pressure) and lower than 20 kg/cm$^2$ (absolute pressure), and when the extraction residue is recycled to the synthesis reaction step, a supplemental amount of the monodentate tertiary amine equal to the amount of the monodentate tertiary amine lost into the extractant may be added to the extraction system to thereby allow the carbonate and/or bicarbonate of said tertiary amine to be formed in the extraction system and fed, as dissolved in the extraction residue, to the reaction system. By this procedure, the concentration of the carbonate and/or bicarbonate of monodentate tertiary amine in the reaction system can be maintained at a constant level. As the monodentate tertiary amine to be added to the extraction system, it is practically advantageous to use the amine separated by distillation or the like from the extract. For example, when triethylamine is used as said monodentate tertiary amine and n-hexane as the extractant, because the two substances are close to each other in boiling point, it is very efficient to distill the extract to recover a mixture of n-hexane and triethylamine and feed it to the extraction system.

The octa-2,7-dien-1-ol as produced by the process of the present invention can be hydrogenated to give n-octanol which is of use as a starting material for the production of plasticizers such as dioctyl phthalate or subjected to oxo and hydrogenation reactions in sequence to give 1,9-nonanediol which is a useful starting material for the production of polyesters with excellent resistance to hydrolysis.

Having generally described this invention, a further understanding can be obtained by reference to certain specific examples which are provided herein for purpose of illustration only and are not intended to be limitative of this invention unless otherwise specified.

EXAMPLE 1

Using the equipment described below, an experimental continuous reaction was carried cut and the reaction data were generated in steady state.

Reaction equipment

A stainless steel autoclave equipped with a temperature controller, stirrer, constant-rate butadiene feed pump, catalyst solution feed pump, reaction mixture feed pump, pressure regulating valve and peeping glass window was used. The reaction mixture was fed to the extraction equipment via a pump and pressure relief valve.

Extraction equipment

A mixer-settler type extraction apparatus equipped with a pressure relief valve, pressure regulating valve, thermometer, stirrer, carbon dioxide gas inlet, constant-rate supplemental liquid feed pump, extractant feed pump and peeping glass window was used. The extraction residue catalyst solution was fed at a constant rate to the reaction equipment by a catalyst solution feed pump through a catalyst reservoir. The extract was fed to the distillation equipment by a feed pump.

Distillation equipment

A supratmospheric pressure distillation equipment for recovering butadiene from the extract by distillation and an atmospheric pressure distillation equipment for recovering a mixture of n-hexane and triethylamine from the residue. The recovered butadiene was returned to a butadiene tank, while the recovered n-hexane-triethylamine mixture was returned to an extractant tank. The n-hexane-triethylamine mixture in the extractant tank was fed to the extraction equipment by an extractant feed pump.

Reaction conditions and results

The composition of the reaction mixture (homogeneous solution) in the reaction equipment at steady state was maintained at 27.6 weight % of sulfolane, 28.3 weight % of water, 9.9 weight % of triethylamine, 0.87 mg atom (as palladium atom)/l of palladium catalyst (formed from palladium acetate), 38.3 mg atoms (as phosphorus atom)/l of organophosphorus compound (lithium diphenylphosphinobenzene-m-sulfonate was employed), 1.68 moles/l of butadiene, and 1.02 moles/l of octa-2,7-dien-1-ol. The operating conditions were: reaction temperature 75° C, reaction pressure 14.3 kg/cm² G[carbon dioxide partial pressure: 10 kg/cm2 (absolute pressure)] and residence time of reaction mixture 0.89 hour. Under the above conditions, the mole ratio of butadiene to octa-2,7-dien-1-ol was 1.65. The above reaction mixture was continuously extracted at a temperature of 25° C. and a pressure of 6 kg/cm² G [carbon dioxide partial pressure: 6 kg/cm² (absolute pressure)] under conditions such that the volume ratio of the reaction mixture to n-hexane was 1.4. The resulting extract was analyzed for the product and the reaction solvent by gas chromatography, for the palladium component by atomic absorption spectrometry and for the phosphorus component by colorimetry. As a result, the concentration of octa-2,7-dien-1-ol in the extract was 0.62 mole/l and the selectivity based on reacted butadiene was 92.2 mole %. Therefore, the production rate of octa-2,7-dien-1-ol was 0.69 mole/l.hr. The amounts of dissolution of the reaction solvent, catalyst, etc. into the extractant were 0.96 mg/l of palladium (on an atomic basis), 2.9 mg/l of phosphorus (on an atomic basis), 8.05 g/l of sulfolane, 2.9 g/l of triethylamine, and 1.02 g/; of water. The equipment was continuously operated for 30 days while the extraction equipment was supplemented with water in an amount equal to the amount consumed in the reaction and palladium acetate, lithium diphenylphosphinobenzene-m-sulfonate and sulfolane in amounts corresponding to the amounts of dissolution of palladium component, phosphorus component and sulfolane into the extractant. It was found that the equipment could be operated stably with constant data and no insoluble polymer was detected in the reaction mixture.

EXAMPLE 2

The same equipment as used in Example 1 was operated under the following conditions. The composition of the reaction mixture (homogeneous solution) in the reaction vessel at steady state: 28 weight % of sulfolane, 28.6 weight % of water, 10 weight % of triethylamine, 1.45 mg atoms (as palladium atom)/l of palladium catalyst (formed from palladium acetate), 61 mg atoms (as phosphorus atom)/; of organophosphorus compound (lithium diphenylphosphinobenzene-m-sulfonate was employed), 0.69 mole/l of butadiene and 0.98 mole/l of octa-2,7-dien-1-ol; reaction temperature: 75° C.; reaction pressure: 14 3 kg/cm² G [carbon dioxide partial pressure: 10.5 kg/cm² (absolute pressure)], and residence time of reaction mixture: 0.9 hour. Under the above conditions, the mole ratio of butadiene to octa-2,7-dien-1-ol was 0.7.

Then, in the same manner as described in Example 1, the above reaction mixture was continuously extracted under conditions such that the volume ratio of the reaction mixture to n-hexane was 1.38 and the extract was analyzed. The concentration of octa-2,7-dien-1-ol in the resulting extract was 0.60 mole/l and the selectivity based on reacted butadiene was 91.6 mole %. Therefore, the production rate of octa-2,7-dien-1-ol was 0.66 mole/±.hr. The amounts of dissolution of the reaction solvent, catalyst, etc. into the extractant were 1.1 mg/l of palladium (on an atomic basis), 3.5 mg/l of phosphorus (on an atomic basis), 7.8 g/l of sulfolane, 3.2 g/±of triethylamine and 1.1 g/l of water. The equipment was operated for 7 consecutive days while the extraction equipment was supplemented with water in an amount equal to the amount consumed in the reaction and palladium acetate, lithium diphenylphosphinobenzene-m-sulfonate and sulfolane in amounts corresponding to the amounts of dissolution of the palladium component, phosphorus component and sulfolane into the extractant. As a result, the equipment could be operated stably with constant data and no insoluble polymer was detected in the reaction mixture.

EXAMPLE 3

The same equipment as used in Example 1 was operated under the following conditions.

The composition of the reaction mixture (homogeneous solution) in the reaction equipment at steady state: 24.2 weight % of sulfolane, 24.2 weight % of water, 8.6 weight % of triethylamine, 1.08 mg atom (as palladium atom)/l of palladium catalyst (formed from palladium acetate), 46.4 mg atoms (as phosphorus atom)/l of organophosphorus compound (lithium diphenylphosphinobenzene-m-sulfonate was employed), 2.525 moles/l of butadiene, and 1.01 moles/; of octa-2,7-dien-1-ol; reaction temperature: 75° C., reaction pressure: 15 kg/cm$^2$ G [carbon dioxide partial pressure: 9.5 kg/cm$^2$ (absolute pressure)]; and residence time of reaction mixture: 0.92 hour. Under the above conditions, the mole ratio of butadiene to octa-2,7-dien-1-ol was 2.5.

Then, in the same manner as described in Example 1, the above reaction mixture was continuously extracted under conditions such that the volume ratio of the reaction mixture to n-hexane was 1.4 and the extract was analyzed. The concentration of octa-2,7-dien-1-ol in the resulting extract was 0.524 mole/l and the selectivity based on reacted butadiene was 92.3 mole %. Therefore, the production rate of octa-2,7-dien-1-ol was 0.67 mole/l.hr. The amounts of dissolution of the reaction solvent, catalyst, etc. into the extractant were 1.2 mg/l of palladium (on an atomic basis), 2.5 mg/l of phosphorus (on an atomic basis), 8.5 g/l of sulfolane, 2.56 g/l of triethylamine and 0.93 g/l of water. The equipment was operated for 2 consecutive days while the extraction equipment was supplemented with water in an amount equal to the amount consumed in the reaction and palladium acetate, lithium diphenyl-phosphinobenzene-m-sulfonate and sulfolane in amounts corresponding to the amounts of dissolution of the palladium component, phosphorus component and sulfolane into the extractant. As a result, the equipment could be operated stably with constant data and no insoluble polymer was detected in the reaction mixture.

EXAMPLE 4

Using the same reaction procedure and the same equipment as Example 1, the extraction was performed at a carbon dioxide partial pressure of 14 kg/cm$^2$ (absolute pressure) and a temperature of 8° C.

The concentration of octa-2,7-dien-1-ol in the extract was 0.61 mole/l and the selectivity based on reacted butadiene was 92.3 mole %. Therefore, the production rate of octa-2,7-dien-1-ol was 0.68 mole/l.hr. The amounts of dissolution of the reaction solvent, catalyst, etc. into the extractant were 0.5 mg/l of palladium (on an atomic basis), 1.54 mg/l of phosphorus (on an atomic basis), 9.0g/±of sulfolane, 1.1 g/l of triethylamine and 0.89 g/l of water. The equipment was operated for 7 consecutive days while the extraction equipment was supplemented with water in an amount equal to the amount consumed in the reaction and palladium acetate, lithium diphenylphosphinobenzene-m-sulfonate and sulfolane in amounts corresponding to the amounts of dissolution of the palladium component, phosphorus component and sulfolane into the extractant. As a result, the equipment could be operated stably with constant data and no insoluble polymer was detected in the reaction mixture.

COMPARATIVE EXAMPLE 1

The same equipment as used in Example 1 was operated under the following conditions. The composition of the reaction mixture (homogeneous solution) in the reaction vessel at 3 days after start-up: 30.5 weight % of sulfolane, 31.2 weight % of water, 10.9 weight % of triethylamine, 1.8 mg atoms (as palladium atom)/l of palladium catalyst (formed from palladium acetate), 76.7 mg atoms (as phosphorus atom)/l of organophosphorus compound (lithium diphenylphosphinobenzene-m-sulfonate was employed), 0.39 mole/l of butadiene, and 0.96 mole/l of octa-2,7-dien-1-ol; reaction temperature: 75° C.; reaction pressure: 15 kg/cm$^2$ G [carbon dioxide partial pressure: 10.5 kg/cm$^2$ (absolute pressure)]; and residence time of reaction mixture: 0.97 hour. Under the above conditions, the mole ratio of butadiene to octa-2,7-dien-1-ol was 0.41.

Then, in the same manner as Example 1, the above reaction mixture was continuously extracted under conditions such that the volume ratio of the reaction mixture to n-hexane was 1.4 and the extract was analyzed. The concentration of octa-2,7-dien-1-ol in the resulting extract was 0.68 mole/l and the selectivity based on reacted butadiene was 88 mole %. Therefore, the production rate of octa-2,7-dien-1-ol was 0.61 mole/;.hr. The amounts of dissolution of the reaction solvent, catalyst, etc. into the extractant were 17.2 mg/l of palladium (on an atomic basis), 4.1 mg/l of phosphorus (on an atomic basis), 7.7 g/; of sulfolane, 3.2 g/; of triethylamine and 1.2 g/l of water. The equipment was operated for 7 consecutive days while the extraction equipment was supplemented with water in an amount equal to the amount consumed in the reaction and palladium acetate, lithium diphenylphosphinobenzene-m-sulfonate and sulfolane in amounts corresponding to the amounts of dissolution of the palladium component, phosphorus component and sulfolane into the extractant. The generated reaction data were gradually deteriorated with time and the amount of dissolution of the palladium catalyst also increased by degrees. The concentration of octa-2,7-dien-1-ol in the extract on the 7th day was 0.61 mole/l and the selectivity based on reacted butadiene was 86.5 mole %. The amounts of dissolution of catalyst, etc. into the extractant were 20.9 mg/; of palladium (on an atomic basis) and 4.28 mg/; of phosphorus (on an atomic basis).

In the reaction mixture withdrawn from the reaction vessel on the 7th day, an insoluble polymer was found.

COMPARATIVE EXAMPLE 2

The same equipment as used in Example 1 was operated under the following conditions.

The composition of the reaction mixture (homogeneous solution) in the reaction equipment at 3 days after start-up: 32.2 weight % of sulfolane, 31.6 weight % of water, 11.4 weight % of triethylamine, 1.35 mg atoms (as palladium atom)/l of palladium catalyst (formed from palladium acetate), 54 mg atoms (as phosphorus atom)/l of organophosphorus compound (lithium diphenylphosphinobenzene-m-sulfonate was employed), 0.22 mole/l of butadiene, and 0.74 mole/l of octa-2,7-dien-1-ol. The operating conditions were: reaction temperature 75° C., reaction pressure 9 kg/cm$^2$ G [carbon dioxide partial pressure: 5 kg/cm$^2$ (absolute pressure)-]and residence time of reaction mixture 1.26 hours. Under the above conditions, the mole ratio of butadiene to octa-2,7-dien-1-ol was 0.3. The above reaction mixture was continuously extracted at a temperature of 20° C. and a pressure of 1 kg/cm$^2$ G [carbon dioxide partial pressure: 1 kg/cm$^2$ (absolute pressure)] under conditions such that the volume ratio of the reaction mixture to n-hexane was 1.43. The concentration of octa-2,7-dien-1-ol in the extract was 0.44 mole/l and the selectivity based on reacted butadiene was 87 mole %. Therefore, the production rate of octa-2,7-dien-1-ol was 0.28 mole/l.hr. The amounts of dissolution of the reaction solvent, catalyst, etc. into the extractant were 1.5 mg/l of palladium (on an atomic basis), 2.9 mg/l of phosphorus (on an atomic basis), 5.6 g/l of sulfolane, 3.3 g/l of triethylamine, and 0.6 g/l of water. The equipment was continuously operated for 3 days while the extraction equipment was supplemented with water in an amount equal to the amount consumed in the reaction and palladium acetate, lithium diphenylphosphinobenzene-m-sulfonate and sulfolane in amounts corresponding to the amounts of dissolution of the palladium component, phosphorus component and sulfolane into the extractant. As a result, the reaction data were gradually deteriorated with time and the amount of dissolution of the palladium catalyst also increased gradually. Moreover, because of the instable interface between the organic and aqueous phases in the extraction apparatus, it was difficult to operate the equipment under stable conditions.

REFERENCE EXAMPLE 1

The influence of the mole ratio of butadiene to octa-2,7-dien-1-ol on the decomposition of octa-2,7-dien-1-ol and formation of an insoluble polymer was investigated. A 500-ml stainless steel autoclave equipped with a sampling port, thermometer, stirrer, carbon dioxide gas inlet and liquefied butadiene inlet with feed pump was charged with 44.8 mg of palladium acetate, 2 g of triphenylphosphine, 90 g of acetonitrile, 25 g of water, 8 g of triethylamine, and 16 g of octa-2,7-dien-1-ol and the internal pressure was adjusted to 5 kg/cm$^2$G [carbon dioxide partial pressure: 5 kg/cm$^2$ (absolute pressure)] with carbon dioxide gas. Then, 2 g of butadiene was introduced to adjust the mole ratio of butadiene to octa-2,7-dien-1-ol to 0.3. The internal temperature was adjusted to 80° C. and the reaction was conducted for 12 hours. The reaction mixture was sampled in small amounts at 30-minute intervals and analyzed for butadiene and octa-2,7-dien-1-ol by gas chromatography. Based on the data, the rate of feed of butadiene was controlled so that the mole ratio of butadiene to octa-2,7-dien-1-ol in the reaction mixture was 0.2 to 0.3. As a result, octa-2,7-dien-1-ol was decomposed at the rate of 9 millimoles/l.hr, mainly into octatriene and octa-1,7-dien-3-ol. The selectivity to octa-2,7-dien-1-ol based on reacted butadiene was 83 mole %. When the contents of the autoclave were inspected at the end of the reaction time, deposits of black insoluble polymer were observed at the level of the reaction mixture.

REFERENCE EXAMPLE 2

An experiment similar to that described in Reference Example 1 was carried out by conducting the reaction for 12 hours, with the mole ratio of butadiene to octa-2,7-dien-1-ol being controlled at 0.9 to 1.0. Under the above conditions, no decomposition of octa-2,7-dien-1-ol was found. Furthermore, the selectivity to octa-2,7-dien-1-ol based on reacted butadiene was 91 mole %. An inspection of the inside of the autoclave revealed no deposit of insoluble polymer.

What is claimed is:

1. A process for the continuous production of octa-2,7-dien-1-ol, which comprises:
reacting butadiene continuously with water in a solvent which is capable of dissolving both reactants in the presence of a palladium catalyst with the mole ratio of butadiene to octa-2,7-dien-1-ol in the reaction mixture being maintained at 0.6 or more while steady state conditions are maintained.

2. The process of claim 1 wherein the mole ratio of butadiene to octa-2,7-dien-1-ol in the reaction mixture is within the range of 0 6 to 2.5.

3. The process of claim 1 wherein the concentration of butadiene in the reaction mixture is 0.6 to 2.0 moles/liter.

4. The process of claim 1 wherein said solvent is an aprotic polar solvent having a dielectric constant in the range of 39 to 100.

5. The process of claim 4 wherein said polar solvent is sulfolane.

6. The process of claim 1, which further comprises, adding to the reaction mixture, a carbonate and/or bicarbonate of a monodentate tertiary amine having a basicity constant (pKa) of 7 or more.

7. The process of claim 6 wherein said tertiary amine is triethylamine.

8. The process of claim 1 wherein the concentration of said palladium catalyst is 0.5 to 5 milligram atoms as palladium atom per liter of the reaction mixture.

9. The process of claim 1, which further comprises, adding to the reaction mixture, a monodentate organophosphorus compound.

10. The process of claim 9 wherein said monodentate organophosphorus compound is a hydrophilic monodentate organophosphorus compound.

11. The process of claim 10, wherein said hydrophilic monodentate phosphine is a compound of the formula:

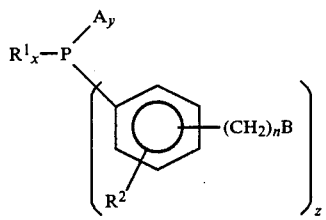

wherein R$^1$ is an aliphatic, alicyclic or substituted or unsubstituted aromatic hydrocarbon group containing 1 to 8 carbon atoms; R$^2$ is a hydrogen atom, a methyl, nitro, cyano or methoxy group, or a halogen atom; n is 0 or 1; x is 0, 1 or 2; y and z are each 0, 1, 2 or 3, provided that y and z are not concurrently equal to 0 and that $x+y+z=3$; A is

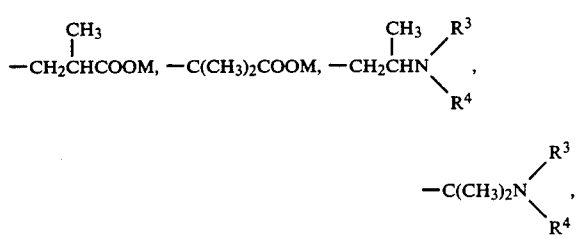

a carbonate or bicarbonate of

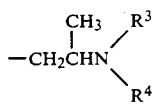

or a carbonate or bicarbonate of

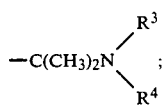

B is —SO₃M,

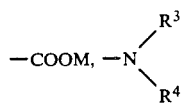

or a carbonate or bicarbonate of

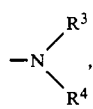

wherein $R^3$ and $R^4$ each represents a methyl, ethyl or n-propyl group; and M is an alkali metal.

12. A process for the continuous production of octa-2,7-dien-1-ol, which comprises:

reacting butadiene continuously with water in an aprotic polar solvent having a dielectric constant in the range of 39–100 and which is capable of dissolving both reactants, with the reaction medium containing a carbonate and/or bicarbonate of a monodentate tertiary amine having a basicity constant (pKa) of at least 7 and a hydrophilic monodentate organophosphorus compound, in the presence of a palladium catalyst with the mole ratio of butadiene to octa-2,7-dien-1-ol in the reaction mixture being at least 0.6 while steady state conditions are maintained;

extracting the reaction mixture continuously with a saturated aliphatic hydrocarbon, a monoolefinic hydrocarbon or an alicyclic hydrocarbon, thereby separating product octa-2,7-dien-1-ol from the reaction mixture; and recycling the extraction residue containing the catalyst component continuously to the reaction mixture.

13. The process of claim 12 wherein the level of addition of said carbonate and/or bicarbonate of monodentate tertiary amine to the reaction system is such that its concentration in the reaction mixture is in the range of 5 to 30 weight percent, the level of addition of said monodentate organophosphorus compound is at least 6 moles per gram atom of palladium, and the reaction is conducted in the homogeneous reaction mixture containing said aprotic polar solvent in an amount such that the weight ratio of water to the aprotic polar solvent in the reaction mixture is in the range f 70/30 through 30/70.

14. The process of claim 13, wherein the extraction is performed under a carbon dioxide partial pressure in the range of 3 kg/cm² (absolute pressure) to 20 kg/cm² (absolute pressure) and at a temperature in the range of 0° to 40° C.

15. The process of claim 14 wherein said monodentate tertiary amine is added to the extraction system in an amount equal to the amount of the monodentate tertiary amine lost by extraction.

16. The process of claim 15 wherein said monodentate tertiary amine is triethylamine, the extractant is n-hexane, the extract is subjected to distillation, and the mixture of n-hexane and triethylamine thus recovered is recycled to the extraction system.

17. A process for the continuous production of octa-2,7-dien-1-ol, which comprises:

reacting butadiene continuously with water in an aprotic polar solvent having a dielectric constant in the range of 39 to 100 and which is capable of dissolving both reactants, with the reaction medium containing a carbonate and/or bicarbonate of a monodentate tertiary amine having a basicity constant (pKa) of 7 or more in the presence of a palladium catalyst and a hydrophilic monodentate organophosphorus compound, thereby synthesizing octa-2,7-dien-1-ol;

continuously extracting the resulting reaction mixture with a saturated aliphatic hydrocarbon, a monoolefinic hydrocarbon or an alicyclic hydrocarbon to separate the octa-2,7-dien-1-ol produced;

continuously adding monodentate tertiary amine to the extraction system in an amount equal to the amount of the monodentate tertiary amine lost during extraction; and continuously recycling the extraction residue containing the catalyst components to said reaction for synthesis of octa-2,7-dien-1-ol, the extraction being conducted under a carbon dioxide partial pressure in the range of 3 kg/cm² (absolute pressure) to 20 kg/cm² (absolute pressure) and at a temperature in the range of 0° C. to 40° C.

18. The process of claim 12 wherein said monodentate tertiary amine is triethylamine, the extractant is n-hexane, the extract is subjected to distillation, and the mixture of n-hexane and triethylamine thus recovered is recycled to the extraction system.

* * * * *